United States Patent
Finke et al.

(10) Patent No.: US 8,196,741 B2
(45) Date of Patent: Jun. 12, 2012

(54) SYRINGE ASSEMBLY AND PACKAGE FOR DISTRIBUTION OF SAME

(75) Inventors: Melvin Finke, DeLand, FL (US);
Jonathan G. Parker, DeBary, FL (US);
John K. Foster, Port Orange, FL (US);
Ellen Morefield, DeLand, FL (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/894,467

(22) Filed: Sep. 30, 2010

(65) Prior Publication Data

US 2012/0080341 A1   Apr. 5, 2012

(51) Int. Cl.
*B65D 83/10* (2006.01)
*B65D 85/20* (2006.01)
*B65D 71/00* (2006.01)
*A47F 7/00* (2006.01)

(52) U.S. Cl. ....... 206/366; 206/443; 206/571; 211/60.1; 211/74

(58) Field of Classification Search .......... 206/364–366, 206/443, 446, 570–572; 211/74, 60.1
See application file for complete search history.

(56) References Cited

U.S. PATENT DOCUMENTS

| | | | | |
|---|---|---|---|---|
| 3,021,942 A * | 2/1962 | Hamilton | ...................... | 206/365 |
| 3,434,587 A * | 3/1969 | Ciampa | ......................... | 206/365 |
| 4,250,998 A * | 2/1981 | Taylor | ........................... | 206/570 |
| 4,349,338 A * | 9/1982 | Heppler | ....................... | 206/364 |
| 4,850,484 A * | 7/1989 | Denman | ...................... | 206/366 |
| 5,190,169 A * | 3/1993 | Sincock | ....................... | 211/60.1 |
| 6,164,044 A | 12/2000 | Porfano et al. | | |
| 6,566,144 B1 | 5/2003 | Madril et al. | | |
| 7,104,400 B2 | 9/2006 | Kiehne | | |
| 7,428,807 B2 | 9/2008 | Vander Bush et al. | | |
| 7,611,012 B2 * | 11/2009 | Ross | ............................ | 206/366 |
| 2002/0069616 A1 | 6/2002 | Odell et al. | | |
| 2008/0244923 A1 | 10/2008 | Yarborough et al. | | |
| 2009/0004063 A1 | 1/2009 | Higashihara et al. | | |
| 2009/0100802 A1 | 4/2009 | Bush et al. | | |
| 2009/0232966 A1 | 9/2009 | Kalyankar et al. | | |

* cited by examiner

*Primary Examiner* — Bryon Gehman
(74) *Attorney, Agent, or Firm* — Lisa E. Winsor, Esq.

(57) ABSTRACT

A package assembly includes a panel, an array of openings defined in the panel, and a plurality of syringe wells. The panel includes an upper surface. Each of the syringe wells is individually associated with a different one of the openings. The panel and the plurality of syringe wells are integrally formed as a unitary structure. Each of the syringe wells is configured to removeably receive a syringe assembly.

8 Claims, 12 Drawing Sheets

US 8,196,741 B2

SYRINGE ASSEMBLY AND PACKAGE FOR DISTRIBUTION OF SAME

BACKGROUND

1. Technical Field

The present disclosure relates to syringes and, more particularly, to medical syringe assemblies such as disposable syringes and prefilled syringes, which include a selectively attachable/detachable plunger rod, and packages for distribution of the same.

2. Discussion of Related Art

A conventional syringe typically includes a hollow barrel configured to slidably receive a plunger having a piston supported on a distal end thereof. The plunger is received in the hollow barrel and partially extends through a proximal end thereof. In use, as the plunger is translated relative to the hollow barrel, the piston is also translated to thereby aspirate and/or dispense fluid into/out of the hollow barrel.

Syringes have been developed for use as disposable syringes that are discarded after a single administration and which include a selectively attachable/detachable plunger assembly. A single-use syringe prevents reuse of the syringe to minimize exposure of patients to HIV, hepatitis and other blood-borne pathogens.

In the case of pre-filled syringes, the syringe is provided with a barrel containing a fluid and with the plunger pre-attached to the barrel. In the instance of relatively large pre-filled syringes, the portion of the plunger extending from the barrel may be relatively large. To reduce the overall length of the pre-filled barrel and plunger, pre-filled syringes have been developed wherein the plunger is selectively attachable/detachable to/from the piston. In this manner, syringes including pre-filled barrels and separate plungers may be stored and shipped at reduced costs.

SUMMARY

A need exists for syringes to be manufactured, sterilized and distributed in a structured configuration suitable for presentation to automated syringe-filling operations.

The present disclosure relates to a package assembly including a panel, an array of openings defined in the panel, and a plurality of syringe wells. The panel includes an upper surface. Each of the syringe wells is individually associated with a different one of the openings. The panel and the plurality of syringe wells are integrally formed as a unitary structure. Each of the syringe wells is configured to removeably receive a syringe assembly.

The present disclosure also relates to a package assembly including a panel and a plurality of syringe assemblies. The panel is formed of a plurality of syringe flanges coupled together in a breakaway configuration. Each syringe assembly of the plurality of syringe assemblies is individually coupled to a different one of the syringe flanges.

The present disclosure also relates to a package assembly including a plurality of syringe packages. Each syringe package includes a connector member and a syringe well coupled to the connector member. The syringe well is configured to removeably receive a syringe assembly. The connector member is configured to releaseably couple adjacent syringe packages to thereby form the package assembly.

BRIEF DESCRIPTION OF THE DRAWINGS

Objects and features of the presently disclosed syringe assemblies and packages for distribution of the same will become apparent to those of ordinary skill in the art when descriptions of various embodiments thereof are read with reference to the accompanying drawings, of which.

DETAILED DESCRIPTION

Figure 1:
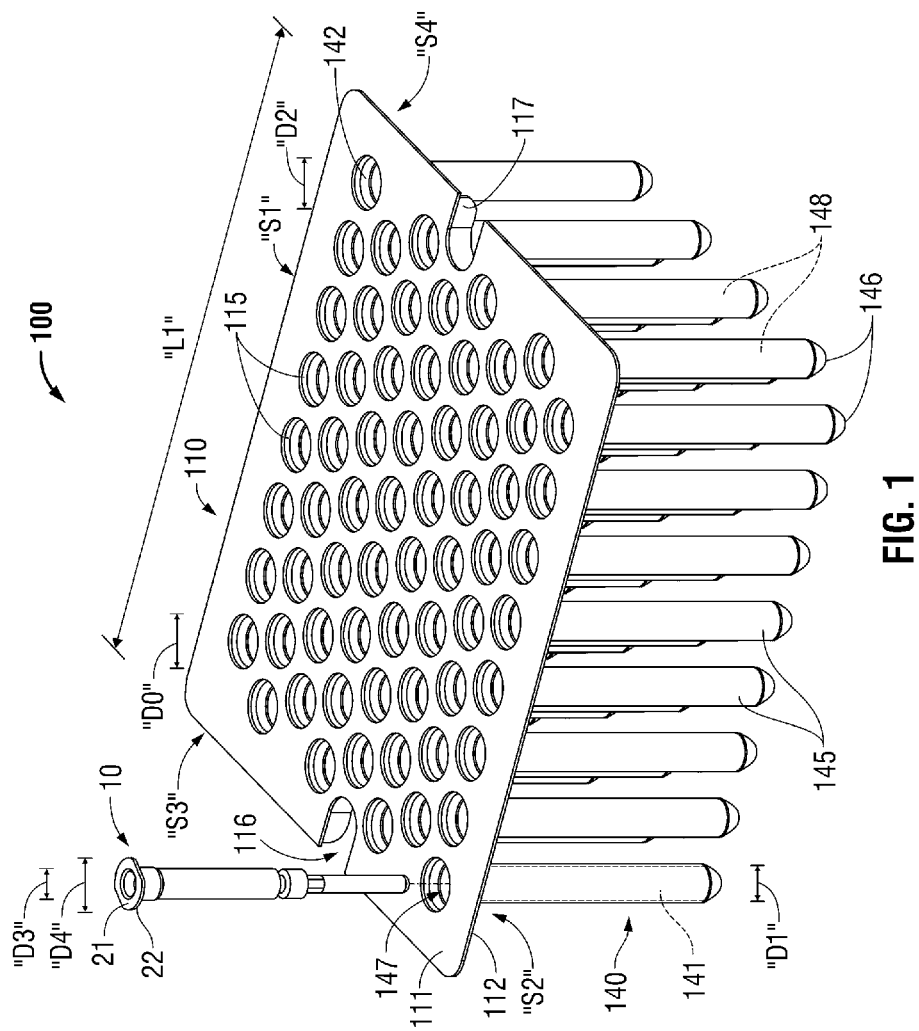
FIG. 1 is a perspective view of a syringe assembly and a package assembly including an array of syringe wells according to an embodiment of the present disclosure.

Hereinafter, embodiments of a syringe assembly and a package for distribution of syringe assemblies of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". As it is used in this description, "plastic" generally refers to any of a wide variety of resins or polymers with different characteristics and uses.

Embodiments of the presently-disclosed syringe assembly are suitable for use as disposable syringes and prefilled syringes. Embodiments of the presently-disclosed package assembly allow syringes to be manufactured, sterilized and distributed in a structured configuration suitable for presentation to automated syringe-filling operations. The teachings of the present disclosure may apply to a variety of syringe assemblies that include a selectively attachable/detachable plunger assembly.

Figure 4:
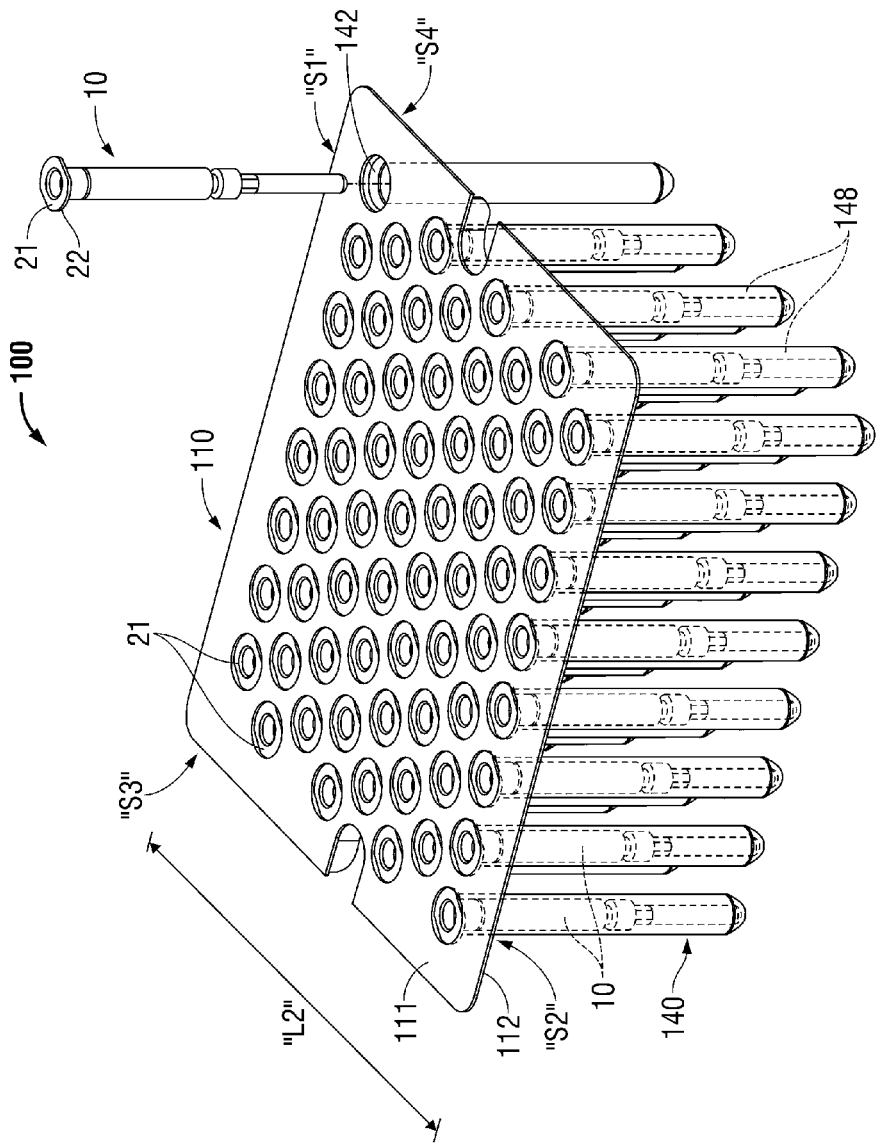
FIG. 4 is a perspective view of the package assembly of FIG. 1 shown with syringe assemblies (in phantom lines) disposed in the array of syringe wells according to an embodiment of the present disclosure.
Figure 5:
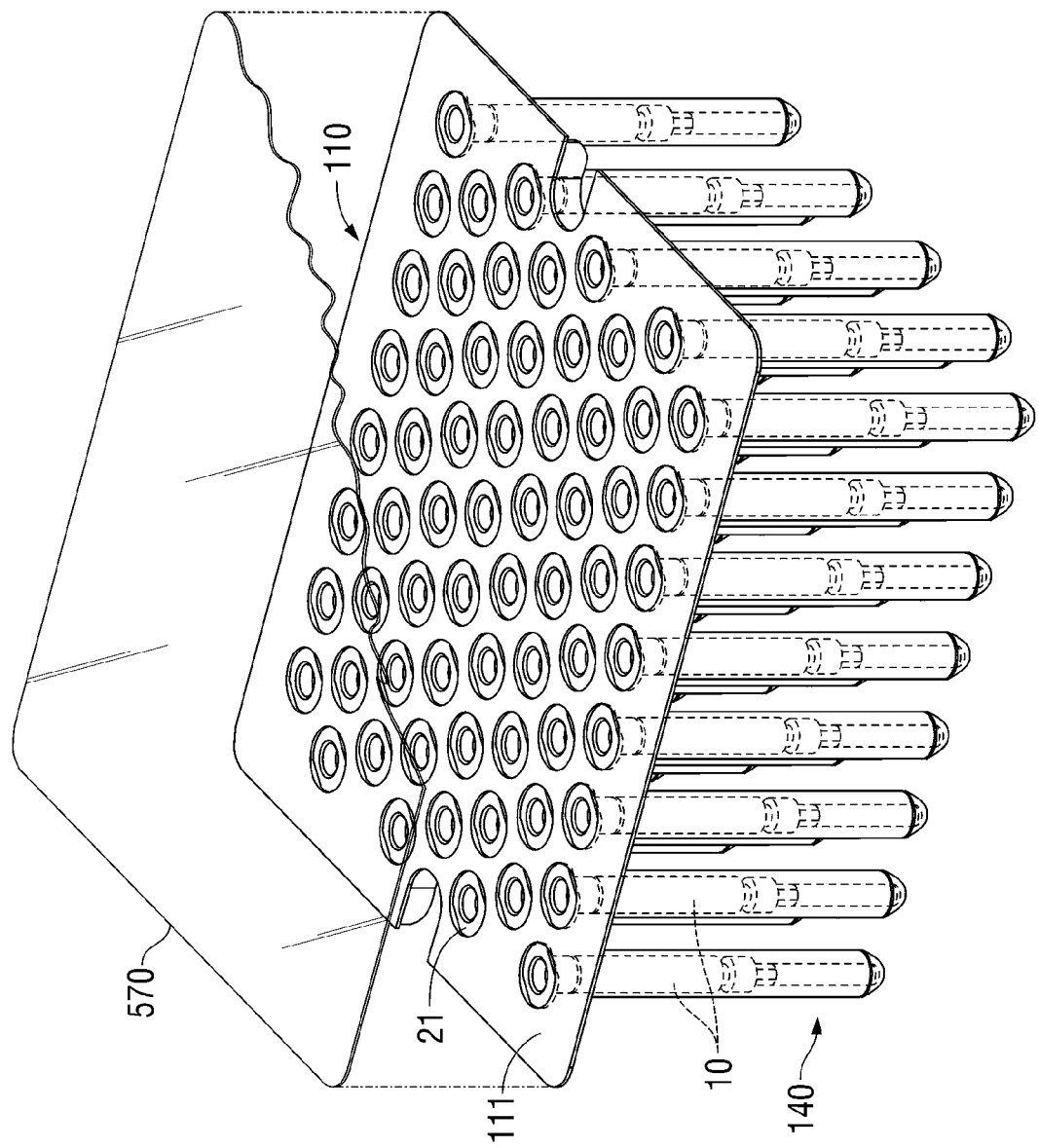
FIG. 5 is a perspective view of the package assembly of FIG. 4 shown with a sterile barrier film according to an embodiment of the present disclosure.

FIGS. 1, 4 and 5 illustrate one embodiment of the presently-disclosed syringe assembly shown generally as 10 and package assembly shown generally as 100. Syringe assembly 10 may be a single-use assembly, which is disposable after use on a subject. Syringe assembly 10, which is described in more detail later in this disclosure, is suitable for use in pre-filled applications.

Package assembly 100 includes a panel 110, an array of openings 115 defined in the panel 110, and a plurality of syringe wells 140, wherein each of the syringe wells 140 is individually associated with a different one of the openings 115. Openings 115 may be arranged in any suitable configuration, for example in a series of rows and/or columns, and may be uniformly spaced apart. Each of the openings 115 has a suitable diameter "D0", and may be configured to allow robotic handling equipment to insert and/or remove the syringe assemblies 10 through the openings 115. Each of the plurality of syringe wells 140 includes an interior cavity 148 of sufficient diameter to removeably receive a syringe assembly 10.

In embodiments, the panel 110 and the syringe wells 140 are integrally formed as a unitary structure by a suitable molding process, such as injection molding. Panel 110 and the syringe wells 140 may be formed by injection-molding devices from suitable polymeric materials, for example, polyolefins such as polypropylene. Syringe wells 140 and/or the panel 110 may be transparent or semi-transparent, which may allow a user to visually inspect the syringe assemblies 10 disposed within the syringe wells 140.

Panel 110 includes an upper surface 111, which may be flat or substantially flat, and a lower surface 112. In some embodiments, the panel 110 has a generally rectangular shape, which may be formed from a first side "S1", a second side "S2", a third side "S3" and a fourth side "S4". It is also envisioned that the panel may assume other configurations, e.g., circular, square, triangle, octagon, etc. As cooperatively shown in FIGS. 1 and 4, the first side "S1" and the second side "S2" have a suitable length "L1", and the third side "S3" and the fourth side "S4" have a suitable length "L2". In some embodiments, the first side "S1" and the second side "S2" are disposed perpendicular to the third side "S3" and the fourth side "S4". Panel 110 may be fabricated from a suitably rigid material. In some embodiments, the panel 110 is formed substantially or entirely from a polymeric material, e.g., plastic.

In some embodiments, one or more cut-out portions 116 are defined in the panel 110, e.g., to facilitate gripping the package assembly 100 and/or to allow the panel 110 to be positionable in a predetermined orientation for syringe filling operations. In one embodiment, panel 110 includes two cut-out portions 116 disposed on opposite sides of the panel 110, e.g., the third side "S3" and the fourth side "S4". Package assembly 100 may include one or more rib elements 117, which may be disposed in proximity to the one or more cut-out portions 116 and configured to provide structural support and rigidity to the panel 110. Rib elements 117 may be coupled to the upper surface 111 of the panel 110 and/or the lower surface 112 of the panel 110. In the embodiment illustrated in FIGS. 1, 4 and 5, the package assembly 100 includes two cut-out portions 116 and two rib elements 117, wherein each rib element 117 has a generally U-like shape and is disposed in proximity to a corresponding one of the cut-out portions 116.

The plurality of syringe wells 140 are generally arranged in a pattern of rows and/or columns. Alternatively, other patterns are envisioned. Openings 115 and the syringe wells 140 may be arranged as nested rows and columns. Each of the plurality of syringe wells 140 includes an open end 147, a closed end 146, and a sleeve body 145, wherein an interior cavity 148 is defined within the sleeve body 145 between the open end 147 and the closed end 146 and disposed in communication with opening 115 in the panel 110. Sleeve body 145 may have a generally cylindrical configuration, and the closed end 146 may have a rounded shape. In the embodiment illustrated in FIGS. 1, 4 and 5, the cavity 148 defined within the sleeve body 145 includes a first portion 141, e.g., a lower portion, having a first diameter "D1", and a second portion 142, e.g., an upper portion (also referred to herein as a "syringe-flange holding area") having a second diameter "D2". In the embodiment shown in FIG. 1, the first diameter D1 is smaller than the second diameter D2. In some embodiments, the first diameter may be substantially identical to the second diameter. In yet other embodiments, the first diameter may be larger than the second diameter which may increase the stability of the syringe assembly package during or after the syringes are loaded. It is also understood that although the openings 115 are shown as circles, they may have any suitable cross sectional shape, such as triangle, square and the like. It is also contemplated that a particular syringe assembly having a predetermined prefilled medicament and/or a predetermined volume of medicament may be assigned to a particular cross sectional configuration of opening 115. For example, a syringe assembly having first medicament at a first volume may be loaded into a platform having circular openings while a syringe assembly having a first medicament at a second volume may be loaded into a platform having octagonal openings. Similarly, a syringe assembly having a second medicament at first volume may be loaded into a platform having a square opening.

Figure 2:
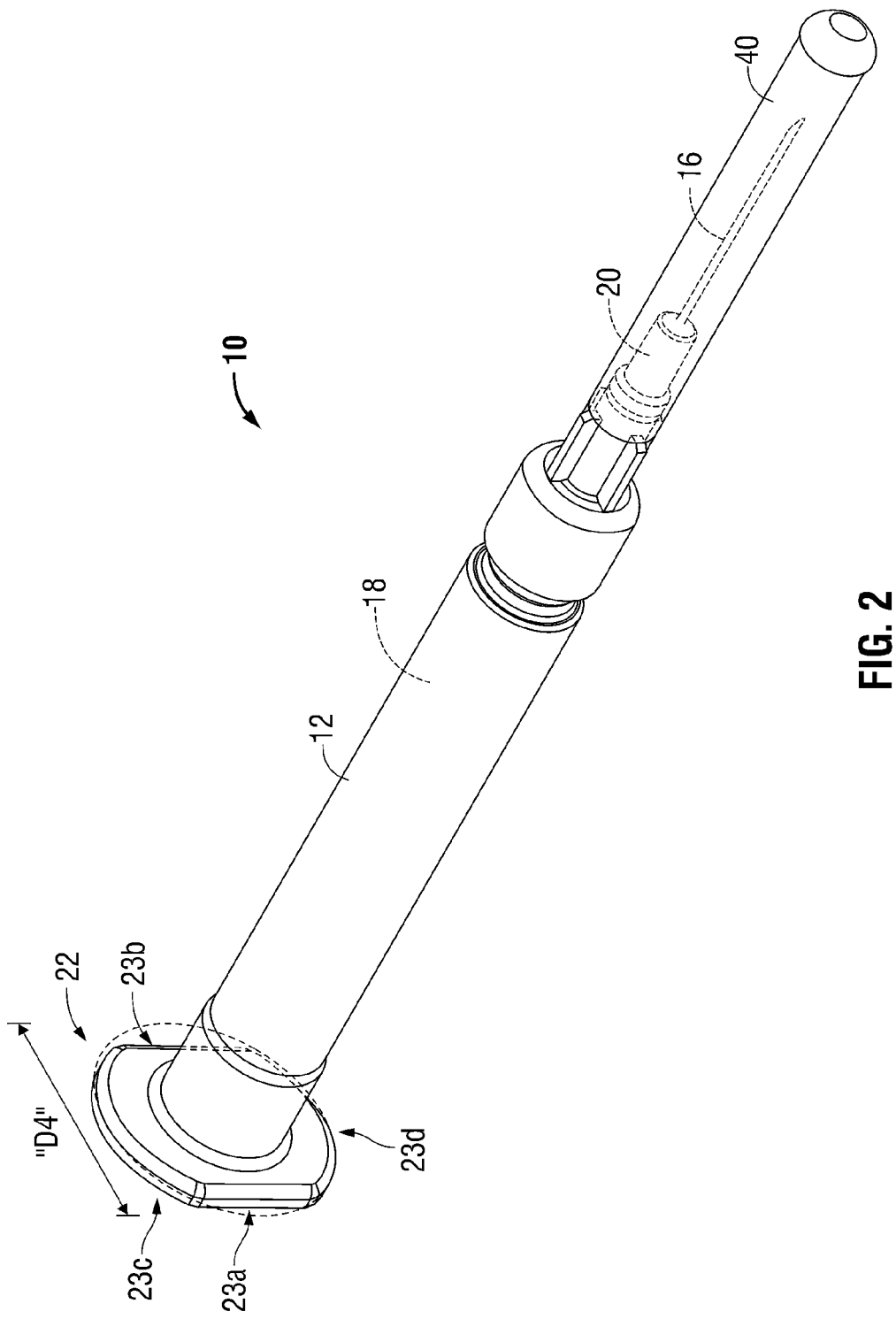
FIG. 2 is an enlarged, perspective view of the syringe assembly shown in FIG. 1 according to an embodiment of the present disclosure.

In FIG. 2, the syringe assembly 10 is shown and includes a syringe body 12, a needle cannula 16 positioned at a distal end of the syringe body 12, and a needle protector or sheath 40. Syringe body 12 defines a fluid chamber or reservoir 18 and includes a distally-positioned needle hub or support 20, which is disposed in fluid communication with the fluid reservoir 18. In some embodiments, the syringe body 12 is made of plastic, e.g., transparent polypropylene. Syringe body 12 may be constructed of nearly any polymeric or glass material. Syringe body 12 has an outer diameter "D3" (shown in FIG. 1). A plunger assembly (e.g., 314 shown in FIG. 3) may be provided for assembly with the syringe body 12.

Fluid reservoir 18 is generally configured to contain a material to be dispensed and/or aspirated. In embodiments, the fluid reservoir 18 may have an internal volume of about 0.3 ml (milliliters) to about 100 ml. Needle 16 may be a stainless steel needle secured within the needle support 20 in a known manner (e.g., by a suitable adhesive) at a distal end of the syringe body 12.

Needle protector or sheath 40 is configured to receive the needle 16 therein and includes an open end configured to be releaseably coupleable with the distal end of the syringe body 12 and a closed end. Sheath 40 may be formed of flexible plastic materials, rigid plastic materials, or other material or materials. Sheath 40 may have a hollow, substantially cylindrical shape. Walls of the sheath 40 may be spaced apart from the needle 16 such that the sheath 40 does not contact needle 16.

Adjacent a proximal end of the syringe body 12 is a peripheral flange 22. Syringe flange 22 includes a proximal end 21 and extends perpendicularly beyond the periphery of the syringe body 12. Syringe flange 22 may be integrally formed with the syringe body 12. In embodiments, the syringe flange 22 has a generally circular shape, as indicated by the dashed circle in FIG. 2. In some embodiments, the syringe flange 22 includes a first lateral edge portion 23a and a second lateral edge portion 23b, wherein the second lateral edge portion 23b is joined to the first lateral edge portion 23a by curved edge portions 23c and 23d. First lateral edge portion 23a and the second lateral edge portion 23b may be disposed in parallel spaced relationship to one another. As shown in FIGS. 1 and 2, the syringe flange 22 has an outer diameter "D4".

Figure 3:
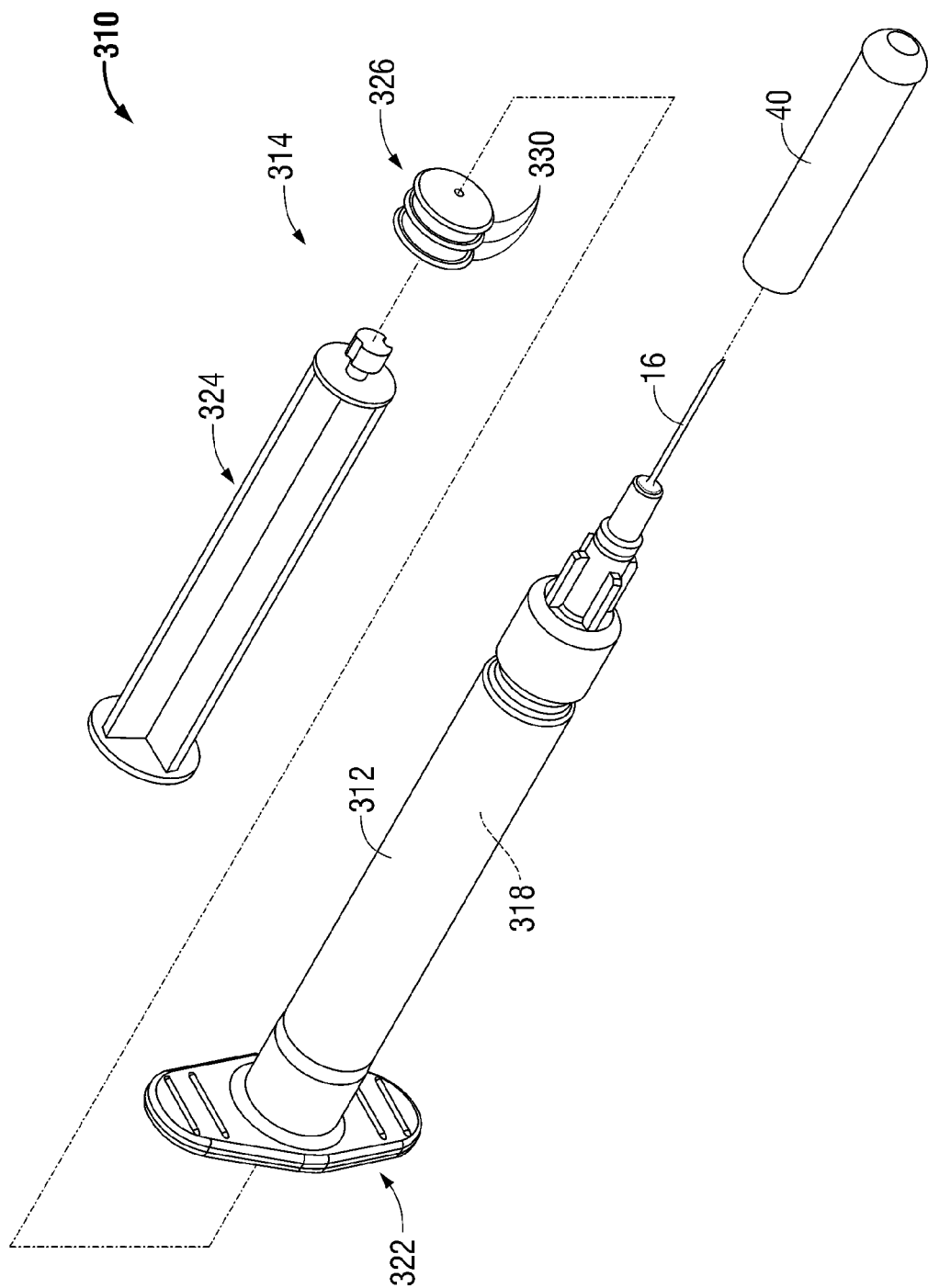
FIG. 3 is an enlarged, perspective view of another embodiment of a syringe assembly including a plunger assembly with parts separated in accordance with the present disclosure.

FIG. 3 shows a syringe assembly 310 in accordance with an embodiment of the present disclosure that includes a syringe body 312, a needle cannula 16 positioned at a distal end of the syringe body 312, a needle protector or sheath 40, and a plunger assembly 314. Syringe body 312 is similar to the syringe body 12 shown in FIG. 2 except for the shape of the syringe flange 322. Plunger assembly 314 includes a plunger rod 324 and a sealing member 326. Plunger rod 324 may include a plurality of vanes extending outwardly from a center longitudinal axis and extending at substantially right angles to each other. In one embodiment, the plunger rod 324 is made of plastic. Sealing member 326 is configured to be slidably received within fluid reservoir 318 of the syringe body 312 and includes one or more annular ribs 330 that sealingly engage an inner wall of syringe body 312 defining reservoir 318. In one embodiment, the sealing member 326 is formed from an elastomeric material.

In FIG. 4, a plurality of the syringe assemblies 10 are shown (in phantom lines) disposed within the syringe wells 140 of the package assembly 100. Syringe assemblies 10 are oriented generally perpendicularly to the generally planar panel 110. Syringe assemblies 10 are loaded into the package assembly 100 such that the distal end of the syringe body 12, covered by the sheath 40, faces the closed end 146 of the syringe well 140 and the proximal end 21 of the syringe flange 22 faces upward. In some embodiments, the syringe flange 22 is positioned in the syringe-flange holding area 142 such that the proximal end 21 of the syringe flange 22 is flush or substantially flush with the upper surface 111 of the panel 110. The proximal end 21 of the syringe flange 22 may alternatively be recessed from the upper surface 111. In one embodiment, the syringe-flange holding area 142 is configured to receive syringe flange 22 in corresponding relation. Alternatively, syringe-flange holding area 142 may be configured to receive flange 322 of syringe assembly 310.

In some embodiments, fluid reservoir 18 is filled with a solution (not shown) before the syringe assembly 10 is loaded into a syringe well 140 of the package assembly 100. In other embodiments, the syringe assembly 10 is loaded into a syringe well 140 before the fluid reservoir 18 is filled with a solution. In certain applications, syringe assembly 10 may contain a flushing solution, e.g., saline or the like. Alternatively, syringe assembly 10 may contain medicinals, including antibiotics, pain medication, therapeutic drugs, heparin or the like.

FIG. 5 shows a sterile barrier film 570 disposed on the upper surface 111 of the panel 110. Barrier film 570 may be adhered to the upper surface 111 of the panel 110 by an adhesive layer (not shown), or other suitable manner of adhesion, welding or the like. Barrier film 570 may be applied to the upper surface 111 of the panel 110 after the syringe assemblies 10 are loaded into the syringes well 140, sterilized, and/or filled with a solution.

Figure 6:
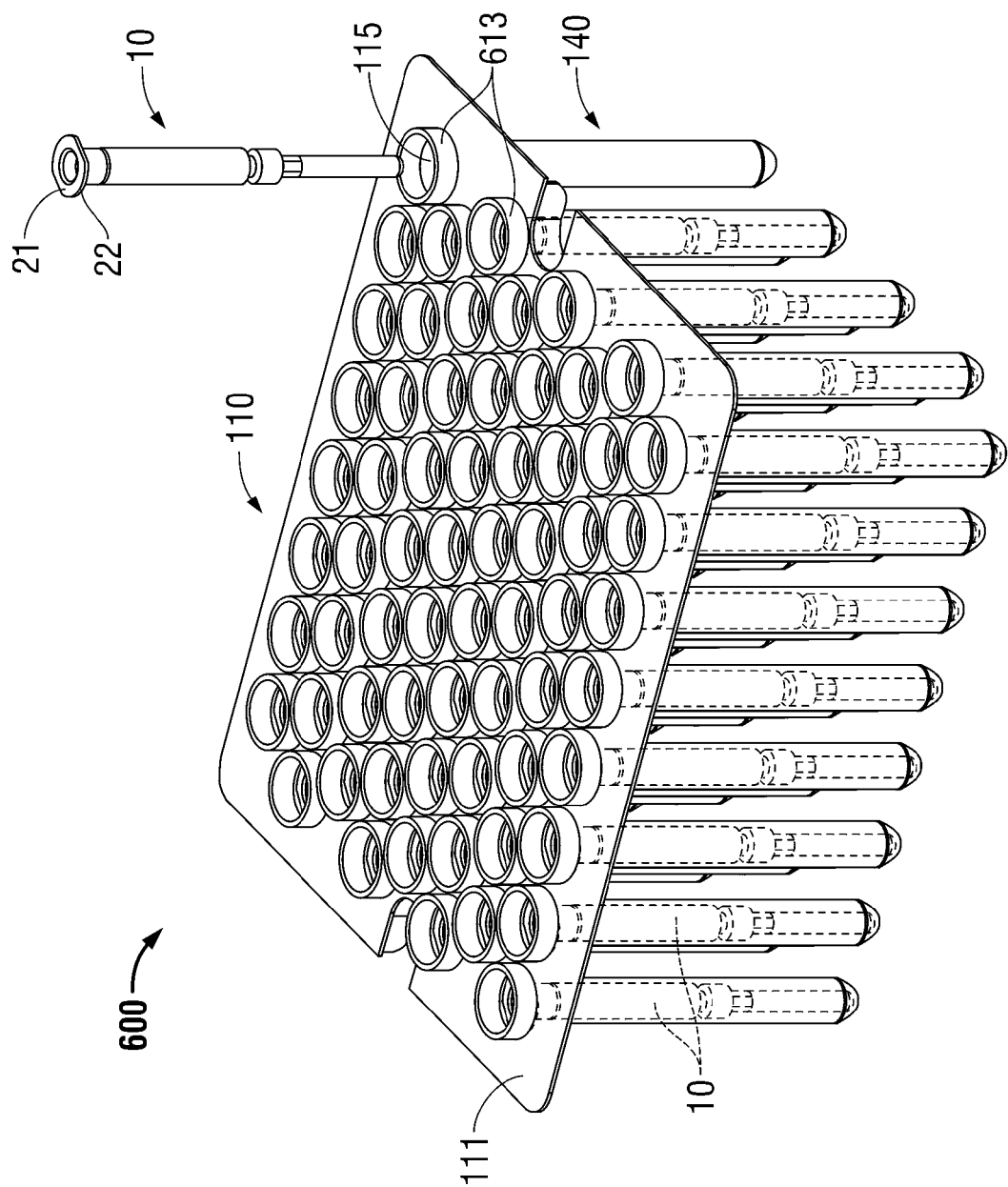
FIG. 6 is a perspective view of a syringe assembly as shown in FIG. 1 and another embodiment of a package assembly in accordance with the present disclosure.
Figure 7:
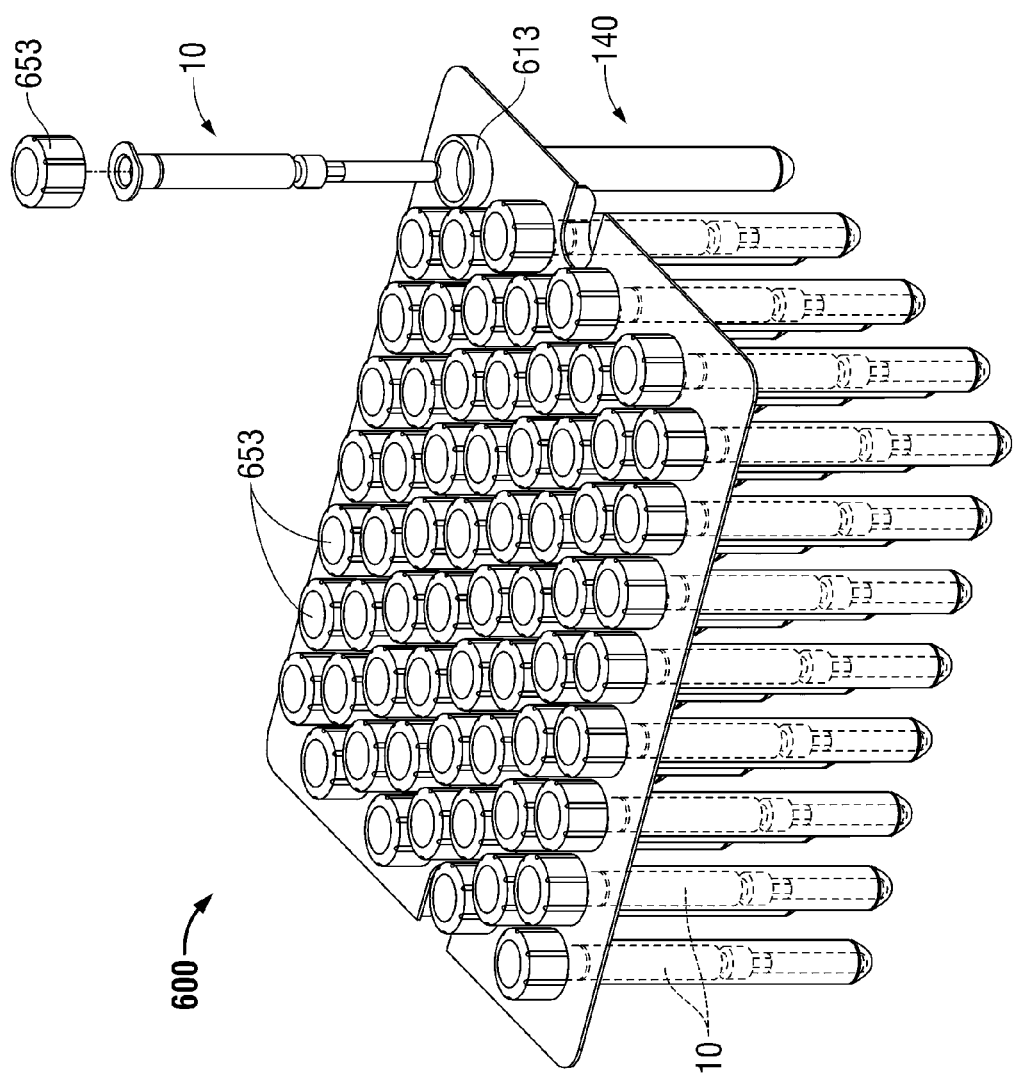
FIG. 7 is a perspective view of the package assembly of FIG. 6 shown with sealing caps according to an embodiment of the present disclosure.

FIGS. 6 and 7 illustrate another embodiment of the presently-disclosed package assembly shown generally as 600. Package assembly 600 includes the panel 110 and the syringe wells 140 of FIG. 1. Package assembly 600 may be formed as a unitary structure of an injection-molded polymeric material. Package assembly 600 is similar to the package assembly 100 of FIGS. 1, 4 and 5 except for a plurality of sealing-cap receiving members 613 coupled to the upper surface 111 of the panel 110 and a plurality of sealing caps 653 (FIG. 7), which are configured to be releaseably coupleable to the sealing-cap receiving members 613. Each of the plurality of sealing-cap receiving members is individually associated with a different opening 115 in the panel 110. Sealing caps 653 may be releaseably connectable to the sealing-cap receiving members 613 by any suitable manner of releasable connection, e.g., snap-fit, press-fit, screw-fit, bayonet-fit, friction fit, releasable adhesive, or other releasable configuration.

Figure 8:
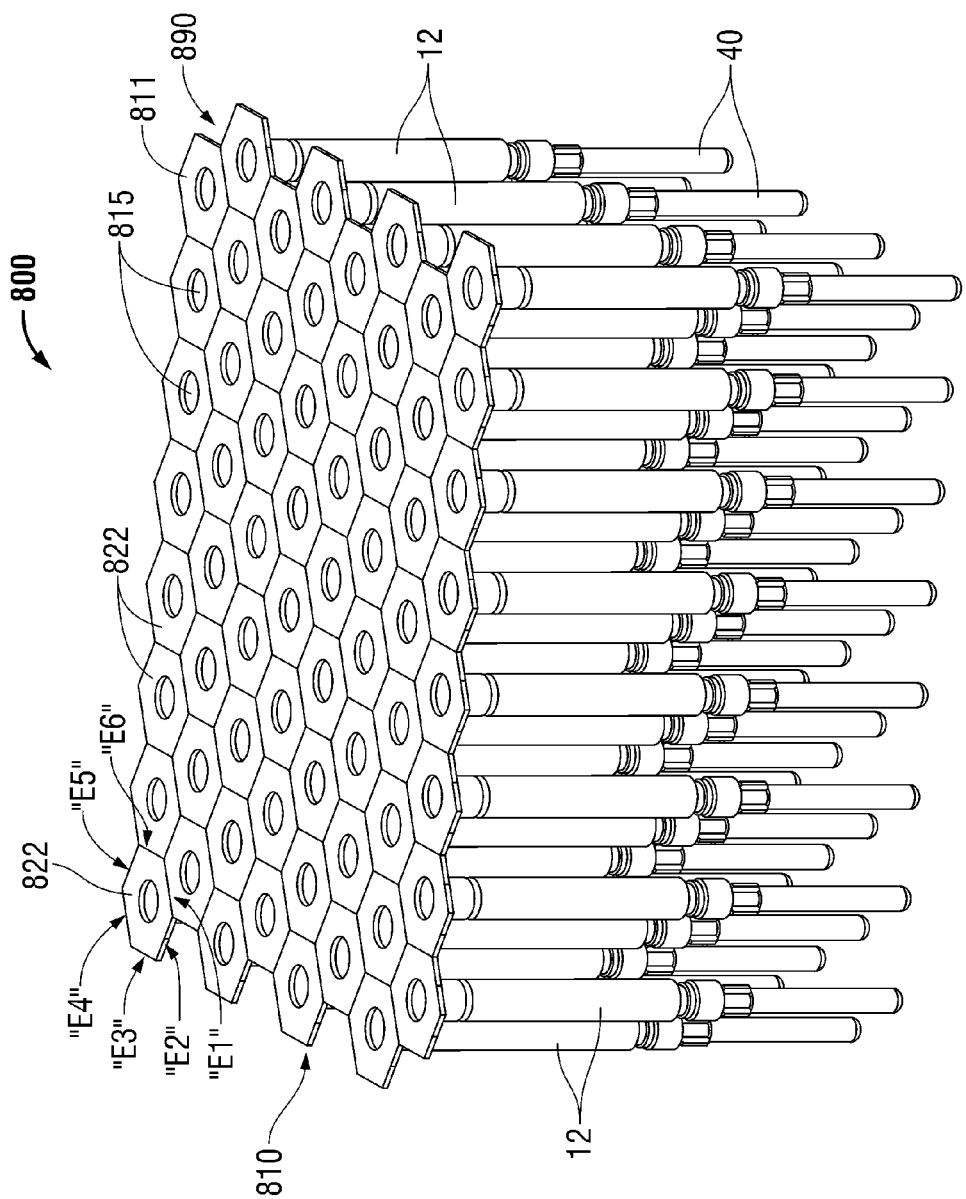
FIG. 8 is a perspective view of a syringe assembly including a flange and a package assembly according to another embodiment of the present disclosure.
Figure 9:
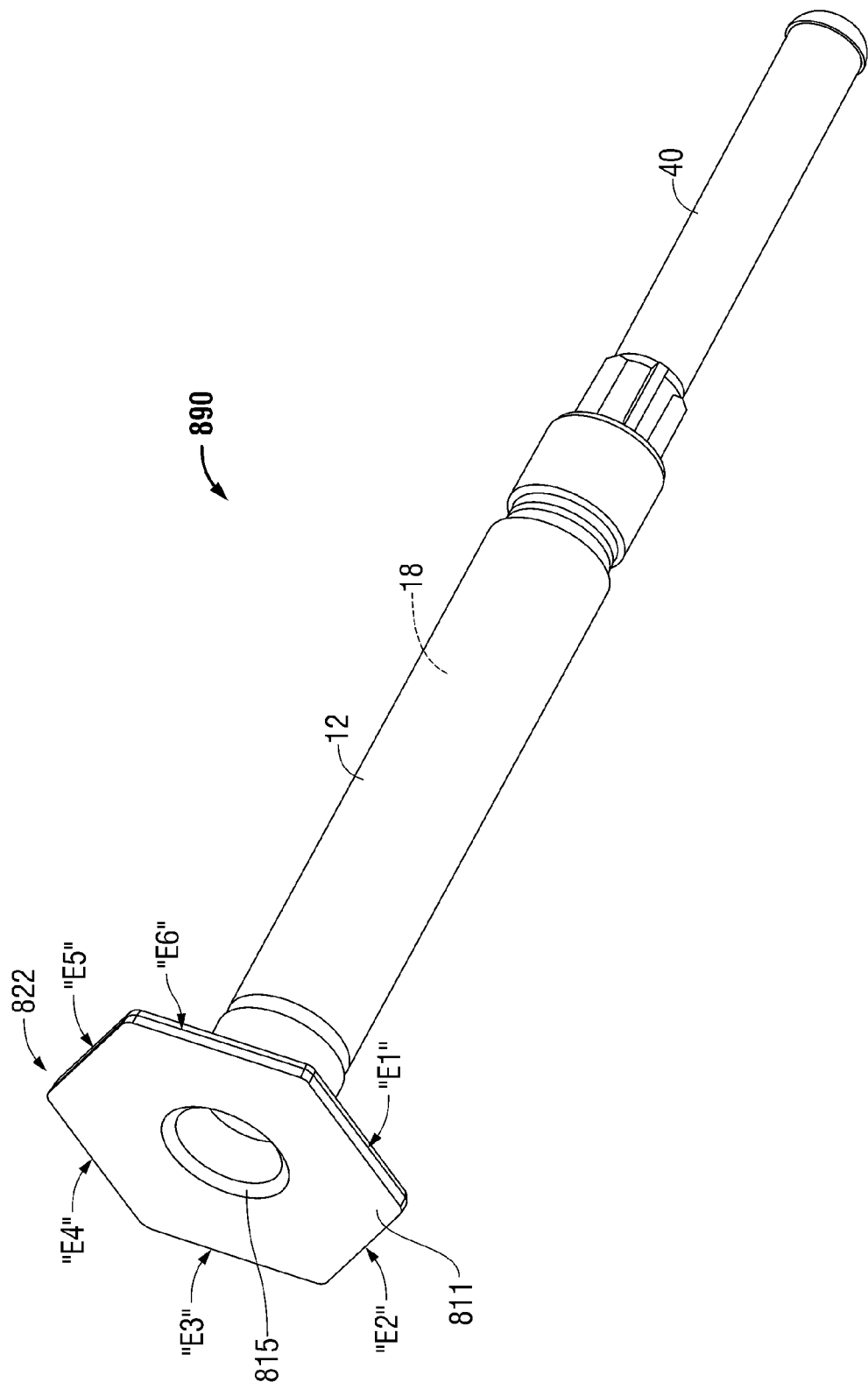
FIG. 9 is an enlarged, perspective view of the syringe assembly shown in FIG. 8 according to an embodiment of the present disclosure.

FIGS. 8 and 9 illustrate an embodiment of the presently-disclosed package assembly shown generally as 800. Package assembly 800 includes a panel 810 formed of a plurality of syringe flanges 822 coupled to one another in a breakaway configuration.

Package assembly 800 includes a plurality of syringe assemblies 890, which are similar to the syringe assemblies 10 of FIG. 2, except for a syringe flange 822. Syringe flanges 822 each define an opening 815 therein and include an upper surface 811. In the embodiment illustrated in FIGS. 8 and 9, each of the syringe flanges 822 includes a first lateral edge "E1", a second lateral edge "E2", a third lateral edge "E3" a fourth lateral edge "E4", a fifth lateral edge "E5" and a sixth lateral edge "E6". In embodiments, the third lateral edge "E3" and the sixth lateral edge "E6" are disposed in a parallel spaced relationship to one another, the first lateral edge "E1" and the fourth lateral edge "E4" are disposed in a parallel spaced relationship to one another, and the second lateral edge "E2" and the fifth lateral edge "E5" are disposed in a parallel spaced relationship to one another. Syringe flanges 822 may be formed of a suitable plastic material, or other material or materials. The number, shape and size of the syringe flanges 822 may be varied from the configuration depicted in FIGS. 8 and 9.

Figure 10:
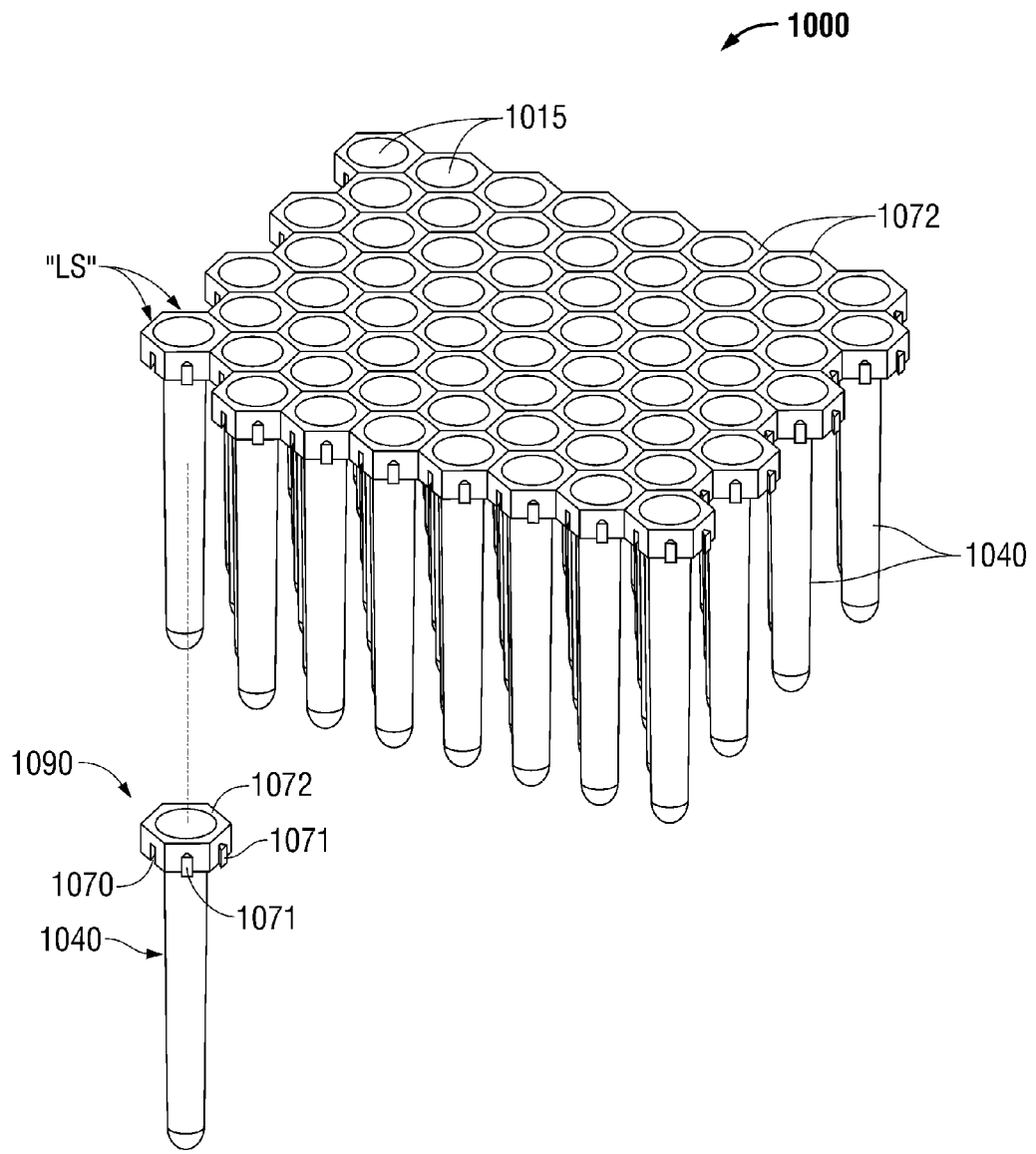
FIG. 10 is a perspective view of another embodiment of a package assembly including an array of syringe packages in accordance with the present disclosure.
Figure 11:
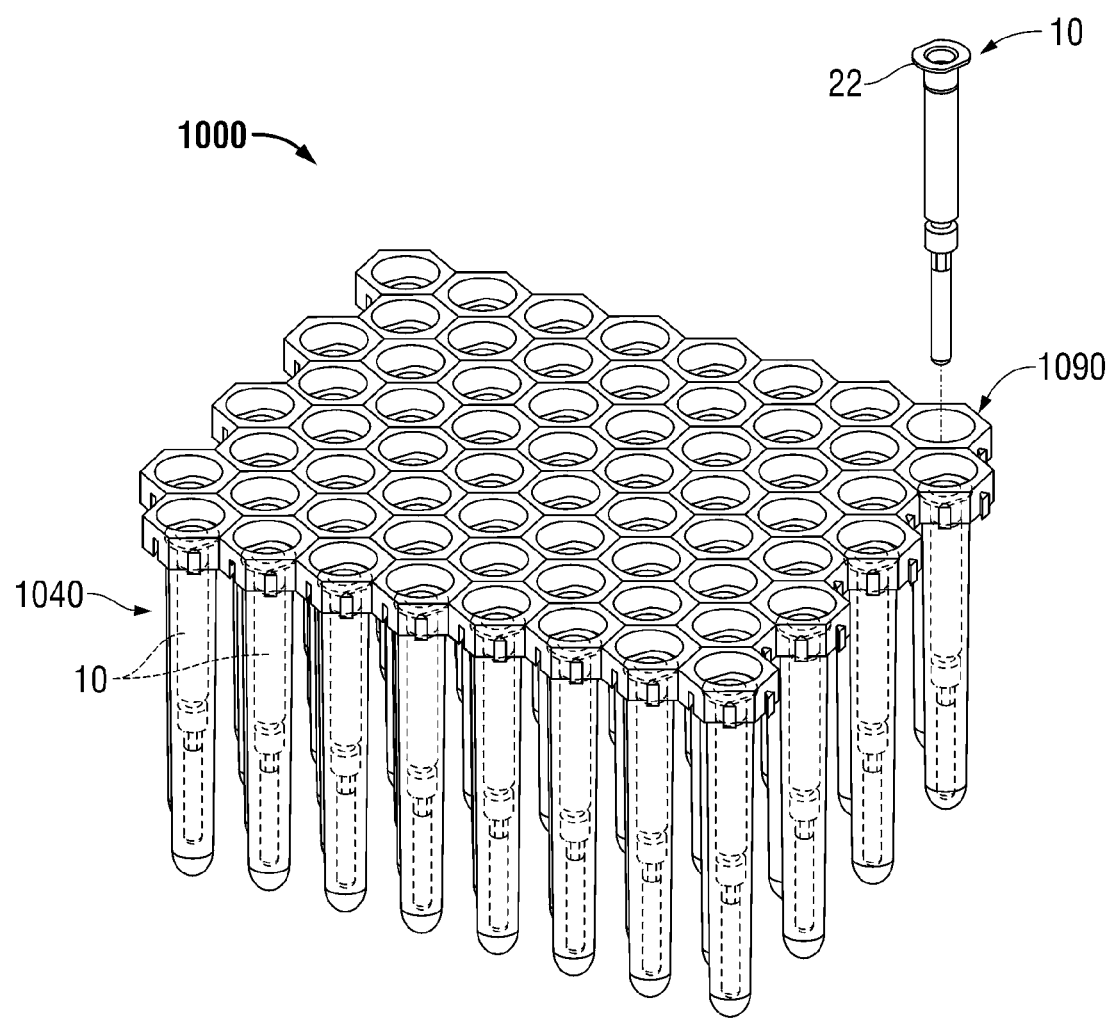
FIG. 11 is a perspective view of the package assembly of FIG. 10 shown with syringe assemblies (in phantom lines) disposed in syringe wells of the array of syringe packages according to an embodiment of the present disclosure.
Figure 12:
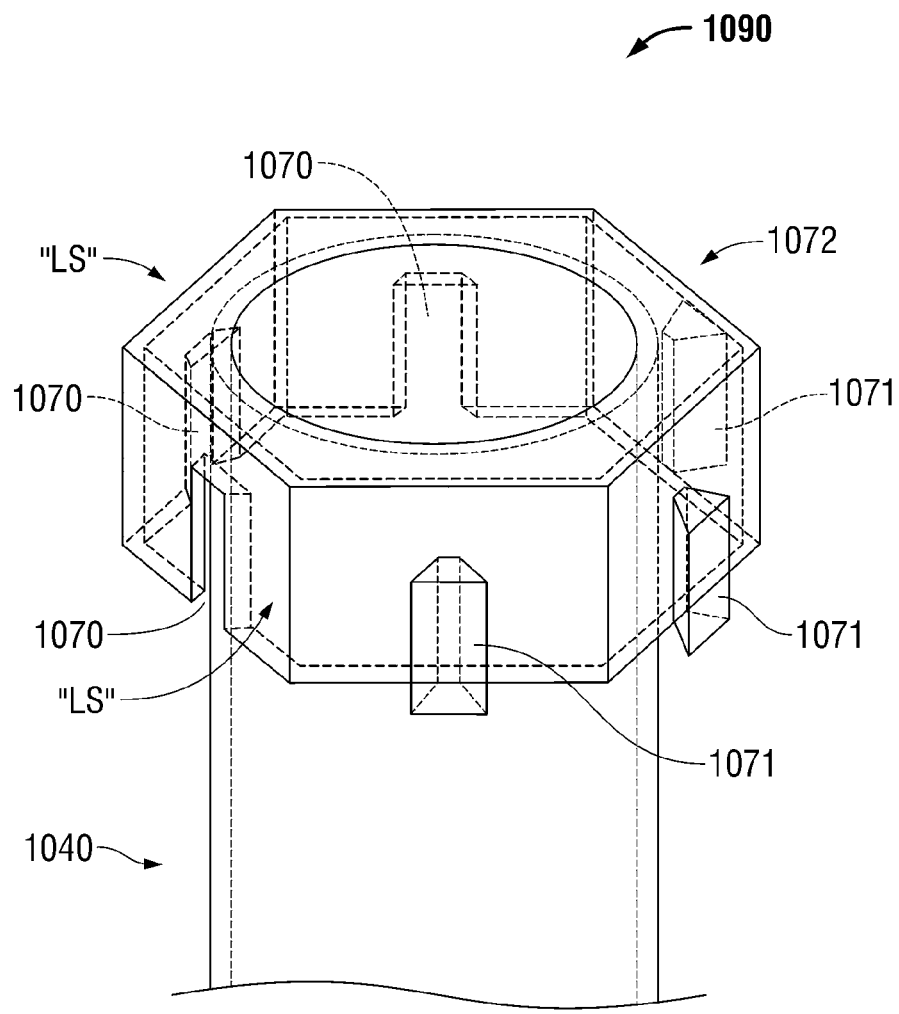
FIG. 12 is an enlarged, perspective view of a connector member of the package assembly of FIG. 10 according to an embodiment of the present disclosure.

FIGS. 10 and 11 illustrate an embodiment of the presently-disclosed package assembly shown generally as 1000. Package assembly 1000 includes a plurality of syringe packages 1090, wherein each of the syringe packages 1090 includes a syringe well 1040 and a connector member 1072. In the embodiment illustrated in FIGS. 10 through 12, the connector member 1072 includes six lateral surfaces "LS", wherein three, adjacent, lateral surfaces "LS" are provided with male-connector elements 1071 and three, adjacent, lateral surfaces "LS" are provided with female-connector elements 1070, which are configured to matingly engage the male-connector elements 1071. In the embodiment shown, each of the male-connector elements 1071 include a triangular dove-tail configuration and the female-connector elements 1070 include correspondingly shaped recesses. Alternatively, other interlocking configurations are envisioned. Additionally, a fewer number of connector elements, e.g., two male connector elements and two female connector elements, may be provided to the connector member 1072.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A package assembly, comprising:
   a panel including an upper surface;
   a plurality of openings defined in the panel,
   a plurality of syringe wells, each syringe well individually associated with a different one of the openings, wherein each of the plurality of syringe wells includes:
   an open end;
   a closed end; and
   a sleeve body disposed between the open end and the closed end, the sleeve body including an upper portion disposed in association with the open end;
   wherein the panel and the plurality of syringe wells are integrally formed as a unitary structure and each of the syringe wells is configured to removeably receive a syringe assembly, the syringe assembly including a syringe flange having a proximal end, wherein the upper portion of the sleeve body defines a syringe flange-holding area configured to support the syringe flange such that the surface of the proximal end of the syringe flange is substantially flush with the upper surface of the panel.

2. The package assembly of claim 1, wherein each syringe well of the plurality of syringe wells further includes:
   a cavity defined within the sleeve body between the open end and the closed end, the cavity disposed in communication with an opening in the panel.

3. The package assembly of claim 2, wherein the cavity includes:
   a first portion having a first diameter; and
   a second portion having a second diameter.

4. The package assembly of claim 3, wherein the first portion of the cavity is configured to receive a syringe body of the syringe assembly therein.

5. The package assembly of claim 3, wherein the second portion of the cavity is configured to receive the syringe flange of a syringe assembly therein.

6. The package assembly of claim 5, further comprising:
   a plurality of syringe assemblies individually disposed within the plurality of syringe wells, wherein each syringe assembly of the plurality of syringe assemblies includes the syringe flange having the proximal end.

7. The package assembly of claim 6, wherein the second portion of the cavity is configured to receive the syringe flange such that the proximal end of the syringe flange is substantially flush with the upper surface of the panel.

8. The package assembly of claim 7, further comprising:
   a sterile barrier film disposed on at least a portion of the upper surface of the panel and configured to cover the plurality of openings in the panel.

* * * * *